United States Patent [19]
Gonzalez-Anguiano Marsel et al.

[11] Patent Number: 5,441,493
[45] Date of Patent: Aug. 15, 1995

[54] DISPOSABLE PANTIES

[76] Inventors: Juan C. Gonzalez-Anguiano Marsel; M. Teresa Fernandez Gonzalez, both of Córcega 659-661, 08026-Barcelona, Spain

[21] Appl. No.: 240,250

[22] Filed: May 10, 1994

[30] Foreign Application Priority Data

Apr. 18, 1994 [ES] Spain .................. 9401024 U

[51] Int. Cl.[6] .............................................. A61F 13/15
[52] U.S. Cl. .................................. 604/394; 604/392; 604/385.1
[58] Field of Search .......................... 604/392–396, 604/385.1

[56] References Cited

U.S. PATENT DOCUMENTS

| | | | |
|---|---|---|---|
| 1,580,464 | 10/1922 | Blumenield | 604/396 |
| 3,424,162 | 1/1969 | Parravicini | 604/396 |
| 3,599,638 | 8/1971 | Rickard | 604/396 |
| 3,599,640 | 8/1971 | Larson | 604/394 |
| 3,613,687 | 10/1971 | Kennedy | 604/396 |
| 4,940,463 | 7/1990 | Leathers et al. | 604/396 |

FOREIGN PATENT DOCUMENTS 1011272  6/1952  France ......................... 604/396

Primary Examiner—Randall L. Green
Assistant Examiner—Rob Clarke
Attorney, Agent, or Firm—Birch, Stewart, Kolasch & Birch

[57] ABSTRACT

The present invention is directed to disposable underpants including an underpant body having an inner surface and an outer surface, a longitudinal undercrotch portion, and front and rear end portions positioned at opposing ends of the longitudinal undercrotch portion and transverse thereto. A sanitary napkin member is positioned over the longitudinal undercrotch portion and extends substantially a length of the longitudinal undercrotch portion, the sanitary napkin including front, rear, and longitudinal edges. The sanitary napkin member is secured to the longitudinal undercrotch portion of the underpant body on the inner surface thereof and only along the rear and longitudinal edges of the sanitary napkin. An increased density of material is provided within the underpant body at the rear end portion thereof and coextensive with the longitudinal undercrotch portion, thus resisting tearing of the rear end portion during flexing of the disposable underpants.

15 Claims, 1 Drawing Sheet (II-II)

DISPOSABLE PANTIES

BACKGROUND OF THE INVENTION

1. Field of the Invention

The present invention relates to improved disposable panties which, in addition to the function for which they are designed, afford a number of advantages discussed hereinafter, and others that are inherent in their organization and construction.

2. Description of Related Art

The market is nowadays known to have underwear such as panties of the disposable type, made using low-cost materials, such as paper, cellulose, unwoven fabric or others, designed to be used for a relatively short period of time, after which they are disposed of.

The use of such panties, currently known in the market, is limited to certain circumstances: trips, extended stays away from home and the like. Though they perform their function in such cases, they have noteworthy disadvantages in those cases where the user must be sent to hospital and/or undergo a surgical operation. Menstrual flows or post-operation process flows are then difficult to control using these or other panties together with traditional sanitary napkins. It is in such circumstances where the use of conventional panties reveals their limitations, in consequence of the duality resulting from the panties and sanitary napkins combination, since these elements are wholly independent from each other and difficult to hold together stably during use, in spite of resorting to adhesive means that are wholly ineffective in practice. A number of problems then arise as a result of an element moving as regards the other: the sanitary napkin becomes loose and moves from its functional position, forming folds in the crotch that are a source of discomfort for the user, which is even greater with secretions and flows, resulting in uncomfortable and unhygienic situations.

In addition to the aforesaid disadvantages, throw-away panties such as those made using a material of uniform thickness are usually torn or severed in areas undergoing a greater strain, such as the rear or backside area. Furthermore, the finish in current panties is deficient, above all in the elastic openings provided for passage of the waist and legs, with the rubber bands usually breaking.

SUMMARY OF THE INVENTION

The applicants for this invention, relying upon their experience in the medical field have devised a number of improvements applicable to panties of the disposable kind, designed in particular for clinical or in-patient use, though their applications can be fully extended to everyday use. The improvements comprise providing the garment or panties with a mini sanitary towel of a particular construction, which is held fast to the panties using permanent attachment means, in order for its functional position to remain unchange during use, the functional position and the size and structure of the towel being carefully studied to provide an optimum service, advantageously correcting all the disadvantages mentioned in the above section and not resolved heretofore.

Now therefore, the object of this invention deals with disposable type panties carrying a mini sanitary towel forming a part thereof, both elements making up an inseparable unit of a hypoallergenic and sterile nature, the towel being sized and positioned in the garment so as to be made the most of, extending between the anal or rear area to the urethral area or pubes at the front part of the user.

The improvements also consider the existence of areas of greater material density and thus have stronger areas in order prevent the garment from tearing or splitting.

The invention provides the advantages described above in addition to others that will follow easily from the embodiment of disposable panties, described hereinafter in detail for an easy understanding of the features set out above, contemporaneously giving a number of details and attaching to the present specification, to such end, some drawings showing a practical example of the object of the present invention that is meant to illustrate and not to limit its scope.

DETAILED DESCRIPTION OF PREFERRED EMBODIMENT

Figure 1:
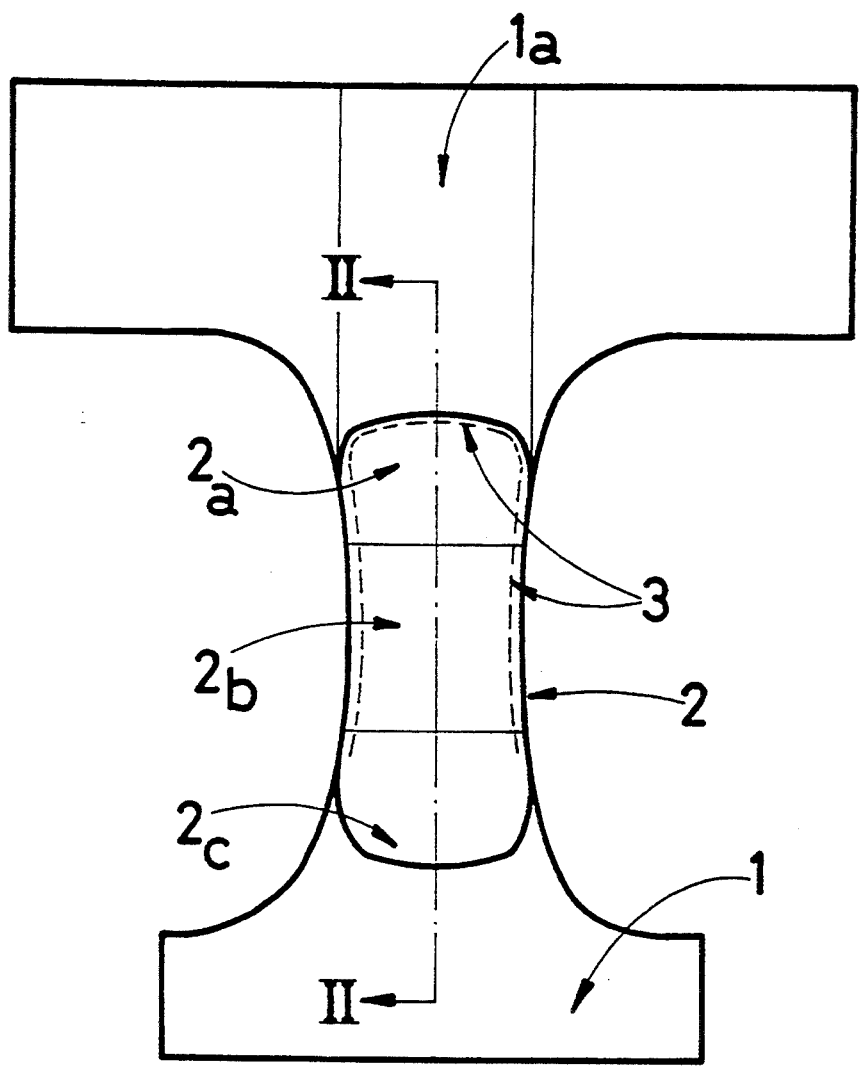
FIG. 1 is an unfolded view of the panties, seen from the front.
Figure 2:
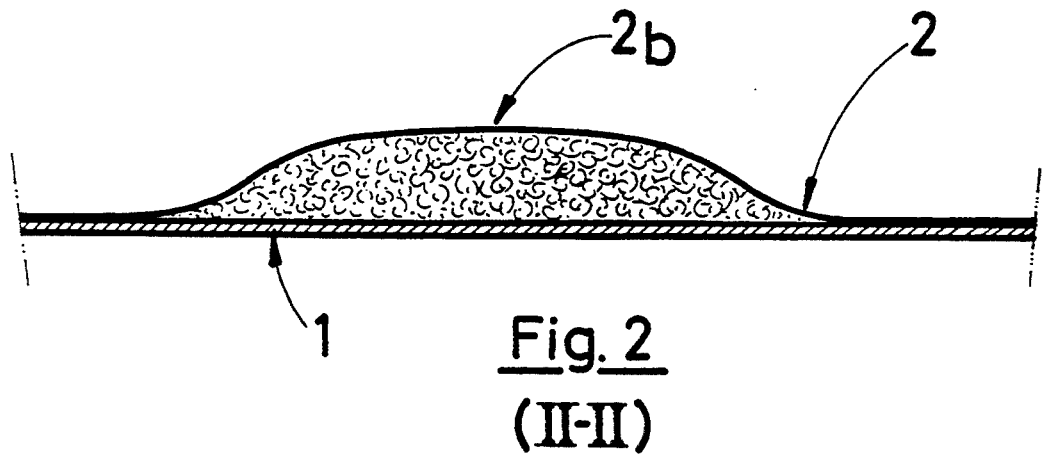
FIG. 2 is a cross-section of the panties, taken along line II—II of FIG. 1.

As shown in the drawings, the disposable panties, carrying the improvements and made in accordance with an embodiment thereof, is of the kind manufactured using a low-cost material, generally numbered 1, for instance paper, cellulose, unwoven fabric and the like.

The main feature of the panties 1 is the provision of a mini sanitary towel 2 absorbing the user's flows and secretions, with both components including panties 1 and towel 2 forming a unit.

The towel 2 is attached to the perineum area of the panties 2 by means of lines of stitches 3 that extend along the longitudinal edges of the towel and its rear edge, leaving a front part, numbered 2c free and a rear part, numbered 2a stitched to the panties 1.

The towel 2 is especially constructed to have a central area 2b that is thicker than the front and rear areas 2c, 2a.

Another advantageous feature of the panties 1 comprises providing a rear surface with a reinforcement material 1a making it more resistent to tear.

We claim:

1. Disposable underpants comprising:
    an underpant body having an inner surface and an outer surface and including a longitudinal undercrotch portion and front and rear end portions positioned at opposing ends of the longitudinal undercrotch portion and transverse thereto;
    a sanitary napkin member positioned over the longitudinal undercrotch portion and extending substantially a length of the longitudinal undercrotch portion, said sanitary napkin including front, rear, and longitudinal edges; and
    means for preventing tearing of said underpant body at the front edge of said sanitary napkin by securing said sanitary napkin to the longitudinal undercrotch portion of said underpant body only at the rear and longitudinal edges thereof.

2. The disposable underpants according to claim 1, further comprising means for providing an increased density of material within said underpant body at the rear end portion thereof and coextensive with the longitudinal undercrotch portion, thus resisting tearing of the rear end portion.

3. The disposable underpants according to claim 1, wherein said underpant body is formed of paper.

4. The disposable underpants according to claim 1, wherein said underpant body is formed of cellulose.

5. The disposable underpants according to claim 1, wherein said underpant body is formed of an unwoven fabric.

6. The disposable underpants according to claim 1, wherein a central area of said sanitary napkin member is thicker than peripheral edges thereof.

7. The disposable underpants according to claim 1, wherein said means for securing is by stitching of said sanitary napkin to the longitudinal undercrotch portion of said underpant body.

8. The disposable underpants according to claim 2, wherein a central area of said sanitary napkin member is thicker than peripheral edges thereof.

9. The disposable underpants according to claim 2, wherein said means for securing is by stitching of said sanitary napkin to the longitudinal undercrotch portion of said underpant body.

10. Disposable underpants comprising:

an underpant body having an inner surface and an outer surface and including a longitudinal undercrotch portion and front and rear end portions positioned at opposing ends of the longitudinal undercrotch portion and transverse thereto;

a sanitary napkin member positioned over the longitudinal undercrotch portion and extending substantially a length of the longitudinal undercrotch portion, said sanitary napkin including front, rear, and longitudinal edges;

means for providing an increased density of material within said underpant body at the rear end portion thereof and coextensive with the longitudinal undercrotch portion, thus resisting tearing of the rear end portion; and means for securing said sanitary napkin member to the longitudinal undercrotch portion of said underpant body on the inner surface thereof and only along the rear and longitudinal edges of said sanitary napkin.

11. The disposable underpants according to claim 10, wherein said underpant body is formed of paper.

12. The disposable underpants according to claim 10, wherein said underpant body is formed of cellulose.

13. The disposable underpants according to claim 10, wherein said underpant body is formed of an unwoven fabric.

14. The disposable underpants according to claim 10, wherein a central area of said sanitary napkin member is thicker than peripheral edges thereof.

15. The disposable underpants according to claim 10, wherein said means for securing is by stitching of said sanitary napkin to the longitudinal undercrotch portion of said underpant body.

* * * * *